ns010441158B2

United States Patent
Thomsen et al.

(10) Patent No.: US 10,441,158 B2
(45) Date of Patent: Oct. 15, 2019

(54) SUPERCONTINUUM LIGHT SOURCE

(71) Applicant: NKT PHOTONICS A/S, Birkerød (DK)

(72) Inventors: Carsten L. Thomsen, Virum (DK); Thomas Vestergaard Andersen, Birkerød (DK); Thomas Feuchter, Holte (DK)

(73) Assignee: NKT PHOTONICS A/S, Birkerod (DK)

( * ) Notice: Subject to any disclaimer, the term of this patent is extended or adjusted under 35 U.S.C. 154(b) by 0 days.

(21) Appl. No.: 15/980,177

(22) Filed: May 15, 2018

(65) Prior Publication Data
US 2018/0360302 A1 Dec. 20, 2018

Related U.S. Application Data

(63) Continuation of application No. 15/283,437, filed on Oct. 2, 2016, now Pat. No. 9,986,904, which is a (Continued)

(30) Foreign Application Priority Data

Jun. 1, 2012 (DK) .................................. 2012 00378
Dec. 18, 2012 (DK) .................................. 2012 70792

(51) Int. Cl.
*A61B 3/00* (2006.01)
*A61B 3/02* (2006.01)
(Continued)

(52) U.S. Cl.
CPC ............ *A61B 3/0008* (2013.01); *A61B 3/102* (2013.01); *A61B 3/1005* (2013.01); *G02F 1/35* (2013.01);
(Continued)

(58) Field of Classification Search
CPC .......... A61B 3/0008; A61B 3/14; A61B 3/12; A61B 3/102; A61B 3/0025
(Continued)

(56) References Cited

U.S. PATENT DOCUMENTS 7,403,688 B2 7/2008 Knox et al.
9,986,904 B2 * 6/2018 Thomsen ................. G02F 1/35
(Continued)

FOREIGN PATENT DOCUMENTS

CN 101371192 A 2/2009
EP 2154566 A1 2/2010
(Continued)

OTHER PUBLICATIONS

Extended European Search Report for European Patent Application No. 13797223.8, dated Jan. 25, 2017.
(Continued)

*Primary Examiner* — Mohammed A Hasan
(74) *Attorney, Agent, or Firm* — Buchanan Ingersoll & Rooney P.C.

(57) ABSTRACT

A supercontinuum light source can include a seed laser arranged to provide seed pulses with a pulse frequency $F_{seed}$; a pulse frequency multiplier (PFM) arranged to multiply the seed pulses by converting pulses having the pulse frequency $F_{seed}$ to pump pulses with a pulse frequency $F_{pump}$, where $F_{pump}$ is larger than $F_{seed}$; and a non-linear element arranged to receive said pump pulses and convert said pump pulses to pulses of supercontinuum light. The PFM can further include a splitter for splitting pulses into first and second sub beams each having the same pulse frequency, where the PFM is configured such that the sub beams experience different delays; and a combiner for combining said first and second sub beams into a beam having the pulse frequency that is greater than said same pulse frequency. The splitter
(Continued)

can have an uneven splitter ratio. The disclosure includes other embodiments as well.

31 Claims, 10 Drawing Sheets

Related U.S. Application Data continuation of application No. 14/404,748, filed as application No. PCT/DK2013/050167 on May 30, 2013, now Pat. No. 9,504,374.

(60) Provisional application No. 61/659,222, filed on Jun. 13, 2012.

(51) Int. Cl.
| | | |
|---|---|---|
| *A61B 3/10* | (2006.01) | |
| *G02F 1/35* | (2006.01) | |
| *G02F 1/365* | (2006.01) | |
| *H01S 5/00* | (2006.01) | |
| *H01S 5/065* | (2006.01) | |
| *G02B 27/09* | (2006.01) | |

(52) U.S. Cl.
CPC ............ *G02F 1/3501* (2013.01); *G02F 1/353* (2013.01); *G02F 1/365* (2013.01); *H01S 5/0092* (2013.01); *H01S 5/0657* (2013.01); *G02B 27/0927* (2013.01); *G02F 2001/3503* (2013.01); *G02F 2001/3528* (2013.01)

(58) Field of Classification Search
USPC ........................................................ 351/221
See application file for complete search history.

(56) References Cited

U.S. PATENT DOCUMENTS

| | | |
|---|---|---|
| 2006/0209908 A1 | 9/2006 | Pedersen et al. |
| 2006/0268393 A1 | 11/2006 | Islam |
| 2007/0086713 A1 | 4/2007 | Ingmar et al. |
| 2007/0216989 A1 | 9/2007 | Nerin et al. |
| 2009/0095890 A1 | 4/2009 | Tanaka |
| 2009/0097512 A1 | 4/2009 | Clowes |
| 2009/0152475 A1 | 6/2009 | Sasaki et al. |
| 2010/0329292 A1 | 12/2010 | Pedersen |
| 2011/0116282 A1* | 5/2011 | Okuno ................ G02F 1/3513 362/551 |
| 2014/0340634 A1 | 11/2014 | Kuranov et al. |
| 2014/0347629 A1 | 11/2014 | Donitzky |

FOREIGN PATENT DOCUMENTS

| | | |
|---|---|---|
| FR | 2 867 574 A1 | 12/2010 |
| JP | 2003121347 A | 4/2003 |
| JP | 2006267071 A | 10/2006 |
| JP | 2007-193231 A | 8/2007 |
| JP | 2008191370 A | 8/2008 |
| JP | 2009037240 A | 2/2009 |
| JP | 2009092570 A | 4/2009 |
| JP | 2009273550 A | 11/2009 |
| WO | 2005041367 A1 | 5/2005 |
| WO | 2007083755 A1 | 7/2007 |
| WO | 2012028152 A1 | 3/2012 |
| WO | 2012076021 A1 | 6/2012 |

OTHER PUBLICATIONS

Decision of Rejection issued by the Japanese Patent Office dated Jan. 9, 2018 in corresponding Japanese Application, 4 pages.
Second Office Action issued by the State Intellectual Property Office of the People's Republic of China in corresponding Chinese Application, dated Nov. 1, 2017,with English translation,14 pages.
Dudley et al. in "Supercontinuum generation in photonic crystal fiber", Rev. Mod. Phys., Dec. 2006, pp. 1159-1162, vol. 78, No. 4.
Lu et al., "Generation of a broadband continuum with high spectral coherence in tapered single-mode optical fibers", Optics Express, Jan. 26, 2004, pp. 347-353, vol. 2, No. 2.
Nishizawa et al., "Super continuum generation for real time ultra-high resolution optical coherence tomography", Proc. of SPIE, 2006, 10 pages, vol. 6102, 6102 H.
Written Opinion {PCT/ISA/237) dated Aug. 8, 2013, by the Danish Patent Office as the International Searching Authority for International Application No. PCT/DK2013/050167.
International Search Report (PCT/ISA/210) dated Aug. 8, 2013, by the Danish Patent Office as the International Searching Authority for International Application No. PCT/DK2013/050167.
Office Action (Examination Search Report) dated Jan. 31, 2019, by the Canadian Intellectual Property Office in Canadian Patent Application No. 2,874,787 (3 pages).
Office Action (Notification of Reasons for Rejection) dated May 28, 2019 by the Japanese Patent Office in rresponding Japanese Patent Application No. 2018-089102 and an English Translation of the Office Action. (8 pages).

* cited by examiner

SUPERCONTINUUM LIGHT SOURCE

CROSS-REFERENCE TO RELATED APPLICATIONS

The present application is a continuation of U.S. application Ser. No. 15/283,437, which was filed on 2 Oct. 2016, which is a continuation of U.S. application Ser. No. 14/404,748, which was filed on 1 Dec. 2014, and which is a national stage application of International Application No. PCT/DK2013/050167, which was filed on 30 May 2013, and which claims the priority of U.S. provisional application No. 61/659,222, which was filed on 13 Jun. 2012, and which claims the benefit of Danish Pat. App. No. PA 2012 00378, which was filed on 1 Jun. 2012 and of Danish Pat. App. No. PA201270792, which was filed on 18 Dec. 2012. The entire contents of each of U.S. application Ser. No. 15/283,437, U.S. application Ser. No. 14/404,748, International Application No. PCT/DK2013/050167, U.S. provisional application No. 61/659,222, Danish Pat. App. No. PA 2012 00378, and Danish Pat. App. No. PA201270792, are hereby incorporated herein by reference in their entirety.

TECHNICAL FIELD

The present invention relates to supercontinuum (SC) light sources as to measurement systems using supercontinuum light sources. Also disclosed are supercontinuum light sources comprising an intermediate supercontinuum light source and a single mode coupling unit, where the supercontinuum light source is suitable for use in a measurement system, for example in a system where a sample to be measured or in other way analyzed is illuminated by light originating from such a supercontinuum light source, where the measurement system is arranged to allow detection of light from the sample. The invention also relates to a system suitable for measuring at least one parameter of an object, said system comprising the supercontinuum light source as well as a method of measuring at least one parameter of an object of the measurement system.

BACKGROUND INFORMATION

Optical measurement systems exist in many variations. Common to these systems is that a beam of light is directed to the sample and light is captured from the sample. The captured light may be light reflected from the sample, transmitted through the sample and/or light emitted from the sample in response to the incoming beam such as fluorescence.

Octave bandwidth supercontinuum (SC) has been successfully generated directly through non-linear fibers, such as microstructured fibers, tapered standard fibers, and tapered microstructured fibers by pumping the fiber with pulsed lasers (often in a MOPA configuration) as input. Such a spectrally broad continuum source is potentially useful in many measurement systems, such as optical coherence tomography (OCT), optical frequency metrology, fluorescent microscopy, coherent anti-Stokes Raman scattering (CARS) microscopy, and two-photon fluorescence microscopy. Unfortunately, for those experiments, the large amplitude fluctuations of conventional continuum sources limit accuracy and/or sensitivity. Previous studies of SC generation have shown that the SC generation process is very sensitive to quantum noise, technical noise, and specific parameters such as the input wavelength, time duration, and chirp of the input laser pulses. A light source derived from a stable continuum would generally improve the usefulness of SC sources.

Continuum generation in conventional holey, photonic crystal, or tapered single-mode long fibers is complex and can contain significant sub-structures in the time and frequency domains leading to undesirable and unevenly distributed noise and instability for different wavelength regions. Usually, the amplitude of the continuum shows large fluctuations with significant excess white-noise background, which can be revealed with a fast detector and RF spectrum analyzer (RFSA) measurement.

A common approach to wavelength conversion is to generate a supercontinuum, then spectrally slice off part of the continuum and use this slice as the light source for the microscopy setup. However, the selected continuum likely contains large amplitude fluctuations (noise), which may not be suitable for some applications.

In U.S. Pat. No. 7,403,688, noise from the SC source is reduced by tapering the non-linear fiber and using a femtosecond pulse source which gives rise to so-called soliton fission. The abstract of this patent states: "The longitudinal variation of the phase-matching conditions for Cherenkov radiation (CR) and four-wave mixing (FWM) introduced by DMM allow the generation of low-noise supercontinuum." Tapering requires either a post processing technique or variation of diameter of the fiber during production which may complicate the production of the SC light source, and the small cross section of a taper may limit the amount of light which can be safely transmitted. Furthermore, femtosecond pump sources are often relatively complex and expensive.

In US2011/0116282 a light source apparatus having a base structure capable of generating SC light and further having a structure that enables the shaping of the spectral waveform of the SC light, power adjustment of the SC light, or adjustment of the frequency of repetition of the pulse train that contains the SC light is described. The light source apparatus of US2011/0116282 comprises a SC fiber pumped at wavelengths at about 1550 nm and the frequency of repetition of a SC optical pulse train from the light source lies between 1 MHz or more, but at 100 MHz or less. Throughout US2011/0116282, noise is only discussed in relation to single pulses, and it is described that the noise characteristic of the pulse light P1 is not influenced. In relation to the noise characteristic of the SC optical pulse train P2, it is mentioned that low noise detection is possible through synchronization with an optical detector disposed outside the light source apparatus. Noise spectra from SC light sources using different pump wavelengths differ, and thus noise suppression may differ. US2011/0116282 refers to femtosecond pulse trains P1. Such pump sources are often relatively complex and expensive.

SUMMARY OF DISCLOSURE

In view of the foregoing, an object of the present invention is to provide a low noise supercontinuum light source and, advantageously, a supercontinuum light source with a reduced impact of noise in the generated supercontinuum (SC). The supercontinuum light source is advantageously suitable for use in an optical measurement system.

In an embodiment, the invention relates to a system suitable for measuring at least one parameter of an object, said system comprising the supercontinuum light source. The invention also relates to providing a method of measuring using the system.

These and other objects have been solved by the invention or embodiments thereof as defined in the claims and as described herein below.

It has been found that the invention and embodiments thereof have a number of additional advantages which will be clear to the skilled person from the following description.

The supercontinuum light source of the invention comprises a light source output, an intermediate supercontinuum light source, and a single mode coupling unit, wherein said intermediate supercontinuum light source comprises
 a. a seed laser arranged to provide seed pulses with a pulse frequency $F_{seed}$;
 b. a pulse frequency multiplier (PFM) arranged to multiply the seed pulses and convert $F_{seed}$ to pump pulses with a pulse frequency $F_{pump}$, where $F_{pump}$ is larger than $F_{seed}$;
 c. a non-linear element arranged to receive said pump pulses and convert said pump pulses to a supercontinuum light provided as an output of said non-linear element and having a supercontinuum spectrum spanning from about $\lambda_1$ to about $\lambda_2$ where $\lambda_1-\lambda_2$>about 500 nm.

The output from the non-linear element is coupled to the single mode coupling unit to provide an output from the single mode coupling unit, and the light source output comprises the output from the single mode coupling unit. The single mode coupling unit is arranged to dampen and shape said supercontinuum spectrum from said non-linear element. Preferably $F_{pump}$ is at least about 100 MHz, such as at least about 150 MHz, such as at least about 200 MHz, such as at least about 300 MHz, such as at least about 400 MHz, such as at least about 500 MHz, such as at least about 600 MHz, such as at least about 700 MHz, such as at least about 800 MHz, such as at least about 1 GHz.

In a preferred embodiment of the frequency multiplier, said single mode coupling unit is arranged to receive said supercontinuum light and spectrally shape it so that the output spectrum from said single mode coupling unit is spanning from $\lambda_3$ to $\lambda_4$, where $\lambda_3-\lambda_4>0$, $\lambda_3 \leq \lambda_1$ and $\lambda_4 \geq \lambda_2$, and wherein the spectrally shaped output spectrum output from the single mode coupling unit is different from the spectrum in the wavelength range from $\lambda_3$ to $\lambda_4$ from the intermediate supercontinuum source.

It has been found that the supercontinuum light source of the present invention has a low-noise resulting in a highly improved supercontinuum light source in particular for applications where low-noise is beneficial. The term "low-noise" is herein taken to mean average noise significantly lower than would otherwise have been possible with prior art white light SC source operating at comparable power level of output power in the spectral range, such as significantly lower than would otherwise have been possible with a prior art supercontinuum light source operating at comparable power level of output power and above the soliton fission regime e.g. when the source is applied in the measurement system.

The seed laser of the intermediate supercontinuum light source can, for example, be a mode-locked fiber laser, preferably mode-locked via a SESAM, preferably the gain medium of said fiber laser is selected from an Yb-doped fiber, an Er-doped fiber and an Er/Yb-doped fiber.

In an embodiment, the wavelength range "$\lambda_3-\lambda_4$" is larger than about 100 nm, such as larger than about 200 nm, such as larger than about 300 nm or such as larger than about 500 nm. In an embodiment, the wavelength $\lambda_4$ is smaller than about 1000 nm, such as smaller than about 900 nm, such as smaller than about 800 nm, such as smaller than about 700 nm, or such as such as smaller than about 600 nm. In an embodiment, $\lambda_3$ is larger than about 1070 nm, such as larger than about 1100 nm, such as larger than about 1200 nm, or such as larger than about 1300 nm.

In an embodiment, the single mode coupling unit comprises one or more of the following: a prism, a low-pass optical filter, a high-pass optical filter, a bandpass optical filter, and a single mode fiber. Advantageously, the single mode coupling unit is arranged to shape the spectrum from the intermediate supercontinuum light source into a Gaussian spectrum, a double peak spectrum or a flat top spectrum.

In an embodiment, the dampening of the supercontinuum spectrum in said single mode coupling unit is given by an optical power dampening factor $\gamma$, said optical power dampening factor $\gamma$ being a measure of the optical power dampening within the wavelength range from $\lambda_4$ to $\lambda_3$, wherein said optical power dampening factor $\gamma$ is larger than about 2, such as larger than about 3, such as larger than about 4, such as larger than about 6, such as larger than about 8, such as larger than about 10.

In an embodiment, the single mode coupling unit comprises at least one of the following in order to carry out said dampening: i) misalignment or mismatch of the output from the non-linear element to the single mode coupling unit; ii) splice loss at the input to and/or output from the single mode coupling unit; and iii) a broadband attenuation filter, such as a neutral density filter or a broadband beam splitter.

In an embodiment, the single mode coupling unit comprises an input for coupling to the non-linear element; a dichroic element at the input of the single mode coupling unit, said dichroic element being arranged to transmit wavelengths below a threshold wavelength $\lambda_5$, wherein $\lambda_5 > \lambda_3$; at least one of the following: a prism, a low-pass optical filter, a high-pass optical filter or a bandpass optical filter; and a single mode fiber, the output of which is the output from the single mode coupling unit. Advantageously, the dichroic element is a single-mode fiber, said single-mode fiber being a step index fiber or a micro-structured fiber comprising micro-structures in the form of air or low-index glass material.

In an embodiment, the total optical power at the output from said single mode coupling unit is less than about 100 mW, such as less than about 50 mW, such as less than about 30 mW, such as less than about 20 mW.

In an embodiment, the seed laser is arranged to provide seed pulses with pulse duration $t_{seed}$, said pulse duration $t_{seed}$ being longer than about 0.1 ps, such as longer than about 0.25 ps, such as longer than about 0.5 ps, such as longer than about 0.75 ps, such as longer than about 1 ps, such as longer than about 2 ps, such as longer than about 3 ps, such as longer than about 5 ps, such as longer than about 10 ps, such as longer than about 20 ps, such as longer than about 50 ps, such as longer than about 100 ps, such as longer than about 200 ps, such as longer than about 300 ps, such as longer than about 400 ps, such as longer than about 500 ps, such as longer than about 1 ns.

In an embodiment, the seed laser is arranged to provide seed pulses with pulse duration $t_{seed}$, wherein said pulse duration $t_{seed}$ is shorter than about 1 us, such as shorter than about 500 ns, such as shorter than about 200 ns, such as shorter than about 100 ns, such as shorter about 50 ns, such as shorter than about 20 ns, such as shorter than about 10 ns, such as shorter than about 1 ns, such as shorter than about 500 ps, such as shorter than about 100 ps, such as shorter than about 50 ps, such as shorter than about 25 ps, such as shorter than about 20 ps, such as shorter than about 15 ps, such as shorter than about 10 ps.

Advantageously, the non-linear element is an optical fiber, such as a tapered and/or untapered micro-structured fiber.

In an embodiment, the intermediate supercontinuum light source comprises a pulse compressor, such as a PBG fiber, said pulse compressor being arranged to receive the pulses from said pulse frequency multiplier (PFM) and to output time-compressed pulses to said non-linear element. Advantageously, the intermediate supercontinuum light source is an incoherent light source.

The system is suitable for measuring at least one parameter on an object, comprises the supercontinuum light source of the invention, and is arranged to illuminate the object to be measured with at least part of an output of said single-mode coupling unit, such as the major part, such as at least about 90%, of all of the output of said single mode coupling unit, the system further comprising a detector for detecting light from said object.

Due to the supercontinuum light source of the invention comprising a low noise intermediate supercontinuum light source, a very accurate optical measurement system is achieved.

In an embodiment, the system comprises the object, and the object is part of a human or animal body, such as a mammalian eye or any part thereof. Hereby, in vivo and/or in vitro measurements of parts of the human or animal body are possible.

Advantageously, the detector has an integration time being longer than the $50/F_{pump}$, such as longer than $100/F_{pump}$, such as longer than $200/F_{pump}$, such as longer than $500/F_{pump}$, such as longer than $1000/F_{pump}$, such as longer than $5000/F_{pump}$.

In an embodiment, the measuring system is a reflection mode measurement system arranged to measure light reflected from said object, such as a system based on white light interferometry, such as Optical Coherence Tomography (OCT). Advantageously, the system is based on time domain, frequency domain or swept source OCT.

In an embodiment, the measuring system is used for diagnosis of Age-related macular degeneration (AMD), diabetic retinopathy or glaucoma.

In an embodiment, the measuring system is used for diagnosis in connection with treatment to correct refractive eye corrections, such as e.g. laser eye surgery to correct refractive eye conditions (LASIK). In an embodiment, the measuring system is used for measuring the boundaries of the Bowman layer inside a human eye.

The method of the invention for measuring at least one parameter on an object to be measured comprises providing a supercontinuum light source of the invention; illuminating the object to be measured with at least part of an output of said single-mode coupling unit of the supercontinuum light source of the invention, such as all of the output of said single mode coupling unit; and detecting light from said object by a detector.

Due to the high accuracy of the optical measurement system the object is advantageously a part of a human or animal body, such as mammalian eye or a part thereof. Hereby, in vivo and/or in vitro measurements of parts of the human or animal body are possible.

In the following the invention will be described in relation to silica-based non-linear fibers; however, as will be clear to the skilled person, the invention will also include SC sources based on other types of non-linear elements such as fibers based on other materials (such as e.g. polymers, chalcogenide and fluoride glasses), non-linear planar waveguides and gas-filled hollow-core fibers. Relative to silica-based fiber parameters, material and/or waveguide based parameters, such as e.g. dispersion and non-linearity, will have to be adjusted accordingly.

Typically, SC is generated by applying a pulsed pump light source arranged to pump a non-linear fiber, such as a non-linear fiber as discussed above. Non-linear processes in the non-linear element convert the pump pulses to a supercontinuum exiting the fiber. Of particular interest is the case where substantial pump energy is provided to wavelengths in the non-linear fiber exhibiting anomalous dispersion since this greatly extends the achievable bandwidth. In particular, supercontinuum generation based on so-called modulation instability where the pump pulse breaks up into a series of short pulses (solitons) which allow the generation of efficient and broad supercontinuum spectra, as described by Dudley et al in Rev. Mod. Phys. Vol. 78, No. 4, (2006). In the normal dispersion regime the supercontinuum generation is caused primarily by self-phase modulation (SPM) which requires very high peak intensity to induce significant spectral broadening (e.g. >100 nm 10 dB bandwidth).

Accordingly, in an embodiment, the pump pulses and the non-linear fiber (i.e. the non-linear element) are arranged so that the supercontinuum spectrum is generated mainly through modulation instability (MI) induced breakup of the pump pulses, i.e. most of the input pulse power is launched at wavelengths situated in the anomalous regime—or sufficiently close to allow initial spectral broadening via SPM to shift a substantial part of the power into the anomalous regime. Preferably more than 50% of the generated supercontinuum spectrum is generated via MI and subsequent processes involving the solitons generated by MI, such as more than 60%, such as more than 70%, such as more than 80% such as more than 90%, such as more than 95%, such as 100%. Any residual pump light exiting the non-linear element is not considered part of the generated supercontinuum. In an embodiment, these percentages are calculated as part of the total power of the supercontinuum. In an embodiment, the percentage is calculated as a percentage of the bandwidth spanned by the supercontinuum.

The high nonlinearity of so called 'Highly Nonlinear Fibers (HNLF) is generally a consequence of relatively small cross sections giving rise to increased peak intensity, but more importantly, the dispersion of these fibers is typically low and anomalous at least for part of wavelength, and the fiber will guide e.g. at the pump wavelength. The former ensures long effective nonlinear interaction length because peak power is maintained, and the latter supports soliton formation and MI breakup. In an embodiment, soliton formation and MI induced breakup are key mechanisms in ultra-broadband light generation from nonlinear fibers. Other nonlinear processes, such as self-phase modulation, cross-phase modulation, self-steepening, Raman scattering, although not requiring anomalous dispersion, also play a part.

The pump pulses and the non-linear element may be arranged so that the center wavelength of the pump pulses is preferably in the anomalous dispersion regime. Alternatively, the pump wavelength could be in the normal dispersion regime but sufficiently close to the anomalous regime that modest spectral broadening can transfer a substantial part of the pump energy to the anomalous regime (e.g. via SPM or Raman shifting), such as more than or equal to ZDW−150 nm, such as more than or equal to ZDW−100 nm, such as more than or equal to ZDW−50 nm, such as more than or equal to ZDW, such as more than or equal to ZDW+10 nm, such as more than or equal to ZDW+20 nm, such as more than or equal to ZDW+30 nm, such as more than or equal to ZDW+50, such as more than or equal to ZDW+100 nm, such as more than or equal to ZDW+150 nm. In an embodiment, the shape of the resulting supercontinuum spectrum can, to a great extent, be controlled by varying the distance from the pump wavelength to the crossing between normal and anomalous dispersion—the so-called zero dispersion wavelength (ZDW).

The term "substantial pump energy shifted into the anomalous region" is taken to mean that more than 30% of the pulse energy enters the anomalous region before the pulse breaks up, such as more than 50%, such as more than 60%, such as more than 70%, such as more than 80% such as more than 90%, such as more than 95%, such as 100%.

As described by Dudley et al. in "Supercontinuum generation in photonic crystal fiber", Rev. Mod. Phys., Vol. 78, No. 4, (2006) pp. 1159-1162 a supercontinuum will be incoherent if modulation instability is the dominating process in the breakup of the pump pulses. An incoherent supercontinuum can be understood as originating from noise and therefore the temporal and spectral stability of the generated light is compromised. According to the authors, pump pulses having a soliton order (N) in the fiber of N<10 provides a coherent supercontinuum, whereas pump pulses having N>30 provides an incoherent supercontinuum. Values of 10≤N≤30 provide a transition between these two states, where a supercontinuum spectrum may be generated coherently or incoherently depending on the exact pump and fiber parameters. Here, the soliton order is defined as (Eq. 1):

$$N = \sqrt{\frac{\gamma \cdot P_0 \cdot T_0^2}{\beta_2}}$$

Where $\gamma$ is the fiber nonlinearity, $P_0$ is the pulse peak power, $T_0$ is the pulse length and $\beta_2$ is the group velocity dispersion of the fiber at the pump wavelength. This equation therefore confirms that short pulses reduce the solitons order providing for a more coherent supercontinuum and thus lower noise.

The coherence may be reduced dramatically (and noise increases dramatically) when N>16. The increased value of N cause modulation instability—which is a pulse breakup induced by quantum noise—to proceed faster than the deterministic soliton fission process. Hence the transition from soliton fission to MI-induced breakup marks the separation between low noise/high coherence and high noise/low coherence. In "Generation of a broadband continuum with high spectral coherence in tapered single-mode optical fibers", Fei Lu, et al., Optics Express, Jan. 26, 2004, vol. 2, No. 2, pp. 347-353 (which is referenced in U.S. Pat. No. 7,403,688 and have authors corresponding to the inventors) short 50 fs pulses provide a relatively low N, and the solitons order is further reduced by tapering providing a high spectral coherence and low-noise. In "Super continuum generation for real time ultrahigh resolution optical coherence tomography", Proc. of SPIE Vol. 6102, 61020H, (2006) supercontinuum is generated using 95 fs pump pulses and it is concluded that only spectra generated by pumping in the normal regime have sufficiently low noise to be applicable. As noted above, such spectra are formed by SPM, which is a deterministic process and thus allows generation of low-noise, highly coherent SC.

In an embodiment, the non-linear fiber is untapered; however, in an embodiment the present invention is combined with the noise reduction effect obtainable via tapering.

Novel types of tapered fibers suitable for SC generation are described in the International Application PCT/DK2011/050328.

However, in an embodiment, the present invention allows the application of incoherent or partially incoherent supercontinuum, so that, in an embodiment, the non-linear fiber and the pump pulses are arranged so that the solitons order of said pump pulses is substantially higher than or equal to 16, such as equal to or more than 18, such as equal to or more than 20, such as equal to or more than 22, such as equal to or more than 24, such as equal to or more than 26, such as equal to or more than 28, such as equal to or more than 30, such as equal to or more than 40, such as equal to or more than 50, such as equal to or more than 75, such as equal to or more than 100, such as equal to or more than 200, such as equal to or more than 300, such as equal to or more than 400, such as equal to or more than 500. Thereby the supercontinuum generation process proceeds mainly via modulation instability.

In an embodiment, the soliton order is defined when the pulse breaks up e.g. after shifting to the anomalous regime and/or after traversing a tapered section of the fiber. In an embodiment, the soliton order is defined at the entry of the pump pulse into the fiber.

Commonly, the spectral width of the generated SC depends on the peak power of the pump pulses, so for longer pulses the peak power cannot be arbitrarily reduced in order to reduce the soliton order. Longer pulses, such as pulses in the ps-regime or ns-regime, are often preferable as these pulses often allow a simpler pump laser design relative to fs-lasers. Accordingly, in an embodiment the invention allows the application of longer pulse durations such as application where the pulse duration is longer than about 0.1 ps, such as longer than about 0.25 ps, such as longer than about 0.5 ps, such as longer than about 0.75 ps, such as longer than about 1 ps, such as longer than about 2 ps, such as longer than about 3 ps, such as longer than about 5 ps, such as longer than about 10 ps, such as longer than about 20 ps, such as longer than about 50 ps, such as longer than about 100 ps, such as longer than about 200 ps, such as longer than about 300 ps, such as longer than about 400 ps, such as longer than about 500 ps, such as longer than about 1 ns, such as longer than about 10 ns.

On the other hand, SC generated from very long pump pulse and CW, pumping suffers from increased noise. While the present invention may reduce sensitivity to noise, it may be preferable to also decrease the noise via reducing pulse duration as well, so that in an embodiment the seed laser is arranged to provide seed pulses with pulse duration $t_{seed}$, wherein said pulse duration $t_{seed}$ is shorter than about 1 us, such as shorter than about 500 ns, such as shorter than about 200 ns, such as shorter than about 100 ns, such as shorter about 50 ns, such as shorter than about 20 ns, such as shorter than about 10 ns, such as shorter than about 1 ns, such as shorter than about 500 ps, such as shorter than about 100 ps, such as shorter than about 50 ps, such as shorter than about 25 ps, such as shorter than about 20 ps, such as shorter than about 15 ps, such as shorter than about 10 ps.

The open-ended intervals mentioned above may be combined to form closed intervals for the pulse duration, such as the pulse duration being between 0.1 ps and 1 μs, such as between 0.25 ps and 100 ps, such as between 1 ps and 50 ps.

As noted above, SC is typically generated by applying a pulsed pump light source. In the supercontinuum light source of the invention, the pump pulses are provided with a repetition rate, $F_{pump}$, which results in an amplitude modulation of the generated supercontinuum with the same frequency, $F_{pump}$. On the other hand, the measurement system of the invention typically applies a measurement time, which is longer than $1/F_{pump}$ over which the measurement is integrated so that the repetition rate is not resolved and the SC appears as CW radiation. Pulsed lasers operating in the MHz range are often referred to as 'quasi CW' for that reason. However, the pulsed nature of the supercontinuum reduces the effective measurement time where light is present. Therefore, in an embodiment the SC light source applies a high repetition rate so that $F_{pump}$ is 100 MHz or more, such as 150 MHz or more, such as 200 MHz or more, such as 300 MHz or more, such as 400 MHz or more, such as 500 MHz or more, such as 600 MHz or more, such as 700 MHz or more, such as 800 MHz or more, such as 1 GHz or more.

As will be further discussed below, a pump laser system typically consists of a master laser oscillator also referred to as a seed laser followed by one or more optional optical amplifiers which boost the power level of the pulses from the seed laser, i.e. the pump laser may comprise a MOPA configuration. Depending on the type of seed laser, it may not be practical or possible to provide such high repetition rates. In an embodiment, the pump laser (also referred to as the pump laser system) comprises a seed laser arranged to provide seed pulses with pulse frequency, $F_{seed}$, lower than $F_{pump}$, and one or more pulse frequency multipliers (PFM) arranged to convert $F_{seed}$ to $F_{pump}$.

Preferably the pulse frequency multiplier of the supercontinuum light source of the invention comprises a splitter dividing at least one beam of the seed pulses into a number of sub beams and a first combiner arranged to recombine at least some of the sub beams. Preferably, the pulse frequency multiplier further comprises an adjustable attenuator arranged to adjust at least one of the sub beams.

A beam herein means a train of pulses.

The splitter may be any kind of splitter. Such splitters are well known in the art.

In an embodiment, the pulse frequency multiplier comprises the adjustable attenuator arranged to receive at least one sub beam. Preferably, the adjustable attenuator is arranged to receive at least one sub beam with a power above average sub beam power, optionally the pulse frequency multiplier comprises a plurality of adjustable attenuators, preferably each arranged to receive at least one sub beam having pulses within a selected peak power range. Advantageously for significantly reducing noise, the adjustable attenuator is arranged to receive and adjust the pulses of the at least one sub beam to a peak power value corresponding to the peak power value of the pulses of at least one other sub beam, such that the pulses of the sub beams combined in the first combiner have substantially identical peak power value.

In an embodiment, the pulse frequency multiplier is configured to time delay at least one of the sub beams. The time delay can e.g. be provided by arranging first a path from the splitter to the combiner of one sub-beam to be shorter than a second path from the splitter to the combiner of a second sub-beam. Preferably, the pulse frequency multiplier is configured to time delay the at least one sub beam such that the pulses of the sub beams recombined in the first combiner are spaced, preferably with a substantially even spacing.

FIG. 1a illustrates the configuration of a preferred intermediate supercontinuum light source 100 being comprised in the supercontinuum light source according to the invention. The master oscillator (or seed laser) provides an output along the beam path 106. The components are preferably fiber coupled but may also be coupled via free-space optics.

The intermediate supercontinuum light source 100 comprises two power amplifiers (PA1 and PA2) 102 and 104. As noted above, these amplifiers are optional, but provide increase in pulse energy and peak power relative to the output from the seed laser 101. The seed laser 101, PA1 102 and PA4 104 are each pumped by diode lasers; however, other pump sources such as an electrical power source could alternatively be used. An optional regulator 105 is included to illustrate that the intermediate supercontinuum light source may comprise a feedback system. A feedback loop is in this embodiment formed by the photo diode 109 measuring a part of the output 108 and providing one or more parameters related to the beam to a decision point 114 which regulates the input to the non-linear element 107. Such a regulator may, as an example, be formed by the adjustable attenuator arranged to adjust the optical power entering the non-linear element 107. Co-pending U.S. patent application Ser. No. 12/865,503 (which is hereby incorporated) discuss various embodiments of feedback loops in SC light sources (see e.g. FIG. 1 and the claims), such as alternative placements of the regulator 105 and the photodiode 109, various embodiments of the regulator, beam collection to the photo diode, and the possibility of applying a feedback response to one or more of the pump sources 110-112.

The PFM 103 may be placed before the first amplifier, between the amplifiers and before the non-linear fiber. In an embodiment, the pulse train saturates the amplifier (PA1 and/or PA2) so that the peak power of the pulses out of the amplifier is constant, regardless of their input power. In FIG. 1, the PFM is placed between two power amplifiers (in this case PA1 and PA2). This may be preferable because in most cases the PFM will redistribute the optical power from the seed laser to a higher number of pulses and may have a significant insertion loss so that if the output pulses of the seed laser are relatively weak, the PFM may produce a pulse train with too low average power for it to be efficiently amplified in a subsequent amplifier. For this reason, it is in an embodiment preferable to place the PFM after one or more amplifiers, such as between two amplifiers. On the other hand, placing the PFM after one or more amplifiers will increase the nominal power lost due to such insertion loss. For this reason, it is in an embodiment preferable to place the PFM before one or more amplifiers, such as between two amplifiers. This may also have the effect of reducing the peak power of the pulses passing one or more power amplifier (or other components in the system), which in turn may have one or more benefits such as reduced non-linearity in the pump laser system. Such non-linearity often has the effect of broadening the pulses, which may result in a reduced peak power level into the non-linear element, which in turn may reduce the spectral width of the generated supercontinuum. In an embodiment, multiple PFMs are applied such as multiple PFMs separated by an optical component such as an optical amplifier, attenuator, compressor or filter.

In an embodiment, there is an upper limit to the allowable average optical power illuminating the object to be measured (also referred to as the sample). Examples of such applications include applications where the object is sensitive to optical power (average power and/or peak power) over a certain threshold—that would be the case for most biological samples—and in specific for parts of a mammalian eye, such as the retina. An example of application where the object is a mammalian eye ophthalmic includes imaging using OCT to image the retina or the cornea and Multiphoton fluorescence microscopy of the retina or the cornea.

In an embodiment, the output of the SC light source or a subsection thereof must conform to one or more of the laser standards Class 1, 1M, 2, 2M, 3R, 3B. In an embodiment, the power of output of the SC source is reduced so that the SC source itself may have a higher output AEL (acceptable emission level) than the above cited classes such as 100% more or higher, such as 200% more or higher, such as 400% more or higher, such as 800% more or higher.

In an embodiment, a relatively low noise induced due to pulse length is desirable so that pulse duration in the range of 0.5 ps-30 ps is preferable, such as pulse duration in the range of 1 ps-20 ps is preferable such as 2 ps-20 ps. In an embodiment, an increased average optical power relative to present systems is not desirable so that the average optical power from the SC source is less than 5 Watt output per ps pulse duration, such as less than 3 Watt output per ps pulse duration, such as less than 2 watt per ps pulse duration, such as less than 1 watt per ps pulse duration. In one embodiment a total average optical power in the visible range (400 nm-850 nm) is arranged to be less than 100 mW, such as less than 50 mW, such as less than 30 mW, such as less than 20 mW. As noted elsewhere, the reduction of average power after output from the SC source is often undesirably complex or impossible as the optical components required to reduce the power alter the spectrum.

As previously noted above, in an embodiment, the spectral width of the generated SC depends on the peak power of the pulses at least to a certain saturation level where further increase of peak power does not increase the spectral width. Also, the conversion efficiency from pump light to SC light depends on peak power, which means that for a fixed pulse width the peak power (and corresponding average power) cannot just be reduced. Below a certain value, the desired spectral width of the generated spectrum will be compromised and eventually, poor conversion efficiency will result in too much unconverted pump light coming through the fiber—which could compromise the sample under observation. Therefore, in an embodiment, a consequence of a minimum peak power, the insertion of a PFM cause an increase in average optical output power relative to the configuration where the PFM is omitted. This occurs because the repetition rate of the pump pulses is increased while the peak power and pulse duration are constant. In an embodiment, the optical power is reduced by adjusting the pump energy provided to the last power amplifier before the non-linear element but as mentioned, this may compromise the resulting spectral width.

In an embodiment, a reduction of average optical power may be performed by introducing a dampening after the non-linear element, such as attenuation or splitting part of the beam away from the beam path. Application requiring a tunable fraction of the generated spectrum directed to the sample may apply an AOTF to perform such function. In an embodiment the AOTF may be controlled so as to reduce the amount of average optical power direct to the sample. For applications requiring broadband illumination, as e.g. in an OCT imaging system, it may be more challenging to apply optical components to the beam without disrupting the shape of the spectrum and/or to damage said optical element. In an embodiment, the pump laser system comprises a pulse compressor, such as a PBG fiber (hollow or solid core), arranged to compress the pump pulses and thus increase peak power. This use of PBG fiber was discussed in the PCT Application WO2005041367. By increasing the peak power of the individual pulse, the use of a pulse compressor will in an embodiment allow the use of a lower average optical power while maintaining the spectral characteristics of the generated spectrum.

In principle, a PFM of the intermediate supercontinuum light source of the invention may be any optical component suitable for receiving a train of pulses at a repetition rate, and convert this input to a train of pulses with a higher repetition rate. In an embodiment, the input and output pulses have substantially the same pulse duration and wavelength. In an embodiment, the PFM functions by splitting the pulse train at the input into a plurality of sub pulse trains which each experience a different delay (optical path length) before being recombined. The relative delay(s) cause(s) a temporal shift of the sub pulse trains when recombined, so that the combined pulse train comprises a higher number of pulses than the input. For example, the input pulse train may be split into two sub pulse trains (or sub beams) where one pulse train is delayed in relation to the other. The repetition rate of the combined train will then be doubled. Preferably, the relative shift between the beams corresponds to half the spacing between two pulses in the input pulse train. In an embodiment, this principle is expanded so that the input beam is initially split into more than two sub beams, such as two, three or four sub beams, each delayed in relation to one another and recombined. It is well-known that optical splitters (or combiners) function in a symmetrical manner. The combination of several optical beams result in the same amount of output beams. In an embodiment, only a single output is used/available, whereas the optical power designated for the other outputs is lost in the optical system. In an embodiment, it is therefore advantageous to cascade couplers/splitters such as discussed in relation to FIG. 2b below.

In an embodiment, the invention relates to a PFM comprising a splitter dividing a beam into sub beams, an optional adjustable attenuator arranged to receive a sub beam, and a first combiner arranged to combine the sub beams. In this way the adjustable attenuator may be adjusted to compensate for production variations in the splitter and/or combiner as well as coupling variations, so that a resulting pulse train of pulses with even peak power may be produced. In an embodiment, the precise adjustment of the peak amplitude is not required, and a substantial difference between the peak power of the recombined sub beams is acceptable.

In an embodiment, one or more splitters and combiners are arranged to have an uneven split ratio (such as $$\frac{x}{1-x}$$

where x is a percentage e.g. 45/55, 40/60, 35/65 or 30/70), and said attenuator is arranged to receive the most powerful sub beam (or the larger contributing sub beam in the combination of the beam), which may ensure that the more powerful sub beam can be attenuated to provide an equal power level as the other sub beam when the sub beams are combined. Thereby the noise is significantly reduced compared with situations where the sub-beam had different power levels.

In an embodiment, the PFM comprises multiple attenuators each arranged to receive a separate sub beam. In an embodiment, the splitter splits the beam into two sub beams. In an embodiment, the splitter splits the beam into more than two sub beam, such as 3 or more, such as 4 or more, such as 5 or more, such 6 or more, such as 7 or more, such as 8 or more. In an embodiment, the first combiner further acts as splitter splitting the combined beam into secondary sub beams followed by a second combiner. In an embodiment, the PFM comprises an adjustable attenuator arranged to receive one of said secondary sub beams. This attenuator may be applied to adjust for variations in the first combiner and second combiner as well as coupling loses and other variations. In an embodiment, the second combiner is arranged to have an uneven split ratio (and thus also an uneven combination of the incoming beams), and the output from said adjustable attenuator is arranged to provide the larger fraction to the output. Again, this may ensure that a pulse train with even power between the pulses can be provided by the PFM.

In an embodiment, the PFM is formed by free-space optics such as bulk beam splitters. In an embodiment, the PFM is formed by fiber optic splitters and/or couplers, which are often preferable in relation to cost and robustness of the system.

DETAILED DESCRIPTION

Figure 1A:
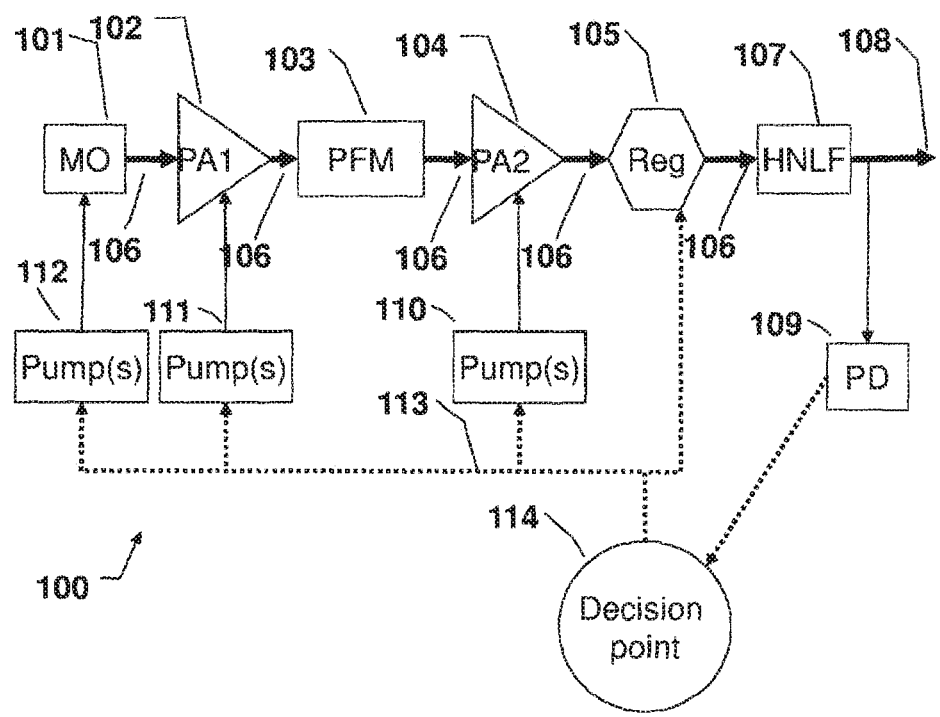
FIG. 1a shows a schematic intermediate supercontinuum light source suitable for the present invention.
Figure 1B:
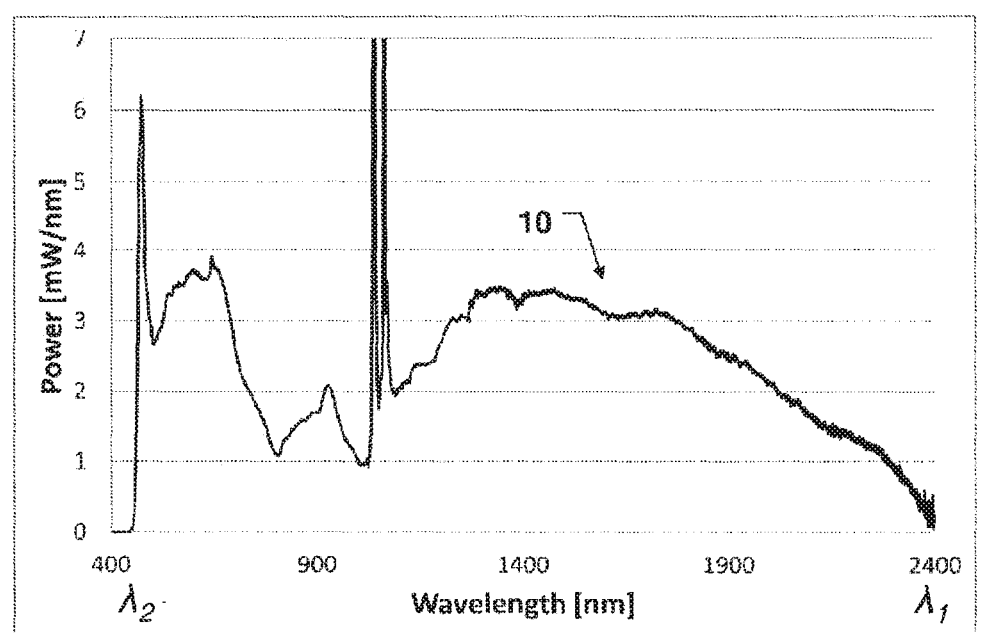
FIG. 1b shows an example of a supercontinuum spectrum (10) spanning from $\lambda_2$ being about 460 nm to $\lambda_1$ being about 2400 nm.

FIG. 1b shows an example of a supercontinuum spectrum (10) spanning from $\lambda_2$ being about 460 nm to $\lambda_1$ being about 2400 nm. The spectrum is obtained from the product SuperK EXW-12 from NKT Photonics A/S.

Figure 2A:
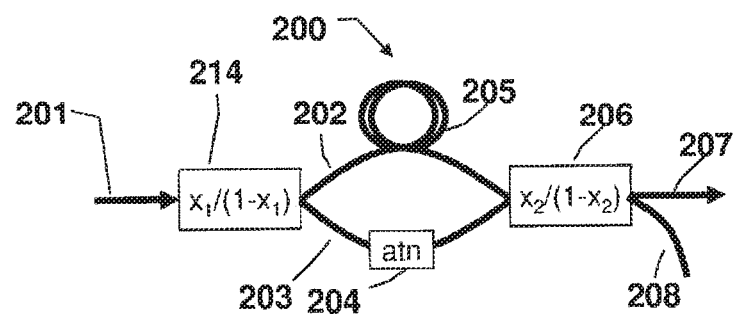
FIGS. 2a and 2b show examples of pulse frequency modulators (PFM) of an intermediate supercontinuum light source according to the present invention.
Figure 2B:
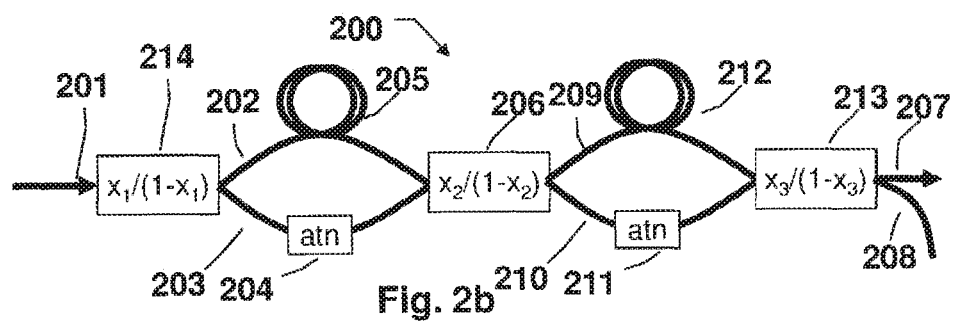

FIGS. 2a and 2b show examples of pulse frequency modulators (PFM) of an intermediate supercontinuum light source according to the present invention FIG. 2a shows an embodiment of a PFM 200. The input beam (either free-space or via a fiber) enters the PFM at the input 201. The splitter 214 is exemplified as a 1×2 splitter but may be any 1×N splitter or even M×N splitter. For an M×N splitter multiple inputs may be combined or alternatively only 1 input of the M available inputs is used. The first splitter 214 divides the input beam into two sub beams 202 203 with a split ratio $x_1/(1-x_1)$. As discussed above, the larger of $x_1$ and $(1-x_1)$ is in an embodiment sent to the adjustable attenuator 204. In an embodiment, the attenuator is omitted in which case it is preferable that $x_1$ is about 0.5 (i.e. 50%) so variations on the peak power of the pulse train at the output 207 may be minimized. The sub beam 202 is subjected to a delay line 205 which is preferably arranged to delay the sub beam 202 with one half of the period between two pulses in the input beam 201. In an embodiment the delay line is adjustable in order to accommodate variations in the repetition rate of the input beam. In an embodiment, small deviations (such as e.g. less than 75%, such as less than 50%, such as less than 25%, such as less than 15%, such as less than 10%, such as less than 5%, such as less than 1%) from an even spacing of the pulses in the output beam can be tolerated so that the delay line is fixed. The sub beams 202 203 are combined at the combiner 206 providing an output 207. The combiner 206 has a split ratio of $x_2/(1-x_2)$. In an embodiment, either the splitter 214 or the combiner 206 is arranged to have an uneven split ratio i.e. either $x_1$ or $x_2$ deviates from 50%, in this way the attenuator 204 may be adjusted so the beams 202 and 203 contribute evenly so that a pulse at the input divided into two pulses is recombined to have substantially the same peak power at the output, where "substantially" means to include what is within the ordinary tolerances. The effect of the PFM is a doubling of the pulse frequency of the input beam. The combiner 206 further has an output 208, which may or may not be a physically available and actual output. However, the output 208 is included to illustrate that the combiner introduces an insertion loss due to the inherent symmetry of a beam splitter/combiner so that the peak power is reduced to about 25% of that of the input when other optical losses (such as in couplings and the attenuator) are ignored. In an embodiment, the beam at the output 208 is applied to monitor the beam and adjust the attenuator 204.

FIG. 2b shows the PFM of FIG. 2a, but further comprising a second coupler 213 so that the PFM provide a quadrupling of the pulse frequency. In principle, a quadrupling could also be obtained by expanding the splitter 214 to a 1×4 and the coupler 206 to a 4×1 coupler. However, the coupler would in this case impose an insertion loss of about 75% due to the symmetry of a beam splitter relative to the loss of about 50% imposed by the second combiner 213. The first delay line 205 is preferably adjusted to one half of the period of the input 201 which results in a doubling of the pulse rate after combining in the combiner 206 and the second delay line 212 is preferably arranged to provide a delay half of that, i.e. one quarter of that of the input at 201. The split ratio $x_2/(1-x_2)$ is in an embodiment arranged to be even where $x_1$ and $x_3$ are arranged to be uneven so that the attenuator 204 may perform the function as described in relation to FIG. 2a and the attenuator 211 may perform a similar function of compensating for variations in the splitting at 206 as well as the combination in the combiner 213. It is notable that further doubling may be obtained by further expanding the PFM by adding couplers without increasing the insertion loss due to symmetric splitting.

Figure 3A:
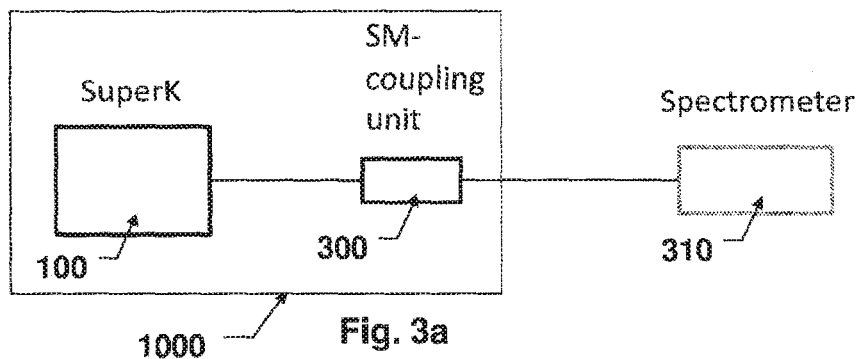
FIG. 3a shows measurement setup suitable for measuring intensity noise in the spectrum of a SC light source, such as that of FIG. 1.

FIG. 3a shows a measurement setup where the SC light source 1000 of the invention is arranged to illuminate a spectrometer rather than an object to be measured. FIG. 3a shows that the supercontinuum light source 1000 of the invention comprises an intermediate supercontinuum light source 100 and a single mode coupling unit 300. The output from the SC light source 1000 is the output from single mode coupling unit 300. The output of the intermediate SC light source 100 is the output from the non-linear element 107 (not shown in FIG. 3*a*). This output from the intermediate SC light source 100 is coupled to the input to the single-mode coupling unit 300. The output of the intermediate SC light source 100 is at least about the output from the non-linear element (107 in FIG. 1*a*) of the intermediate supercontinuum light source (100 in FIG. 1*a*; not shown in FIG. 3*a*). The single mode coupling unit 300 comprises an adaptation in the form of dampening and/or shaping the spectrum according to the requirements of the application. In one embodiment the SM coupling unit 300 comprises one of the embodiments of co-pending PCT application PCT/DK2011/050475 (hereby incorporated), see in particular the embodiments relating to FIGS. 5*a*, 6, 7, 8-10, 13-15, and 17-19 as well as their variations as well as any one of the items and/or claims.

Figure 3B:
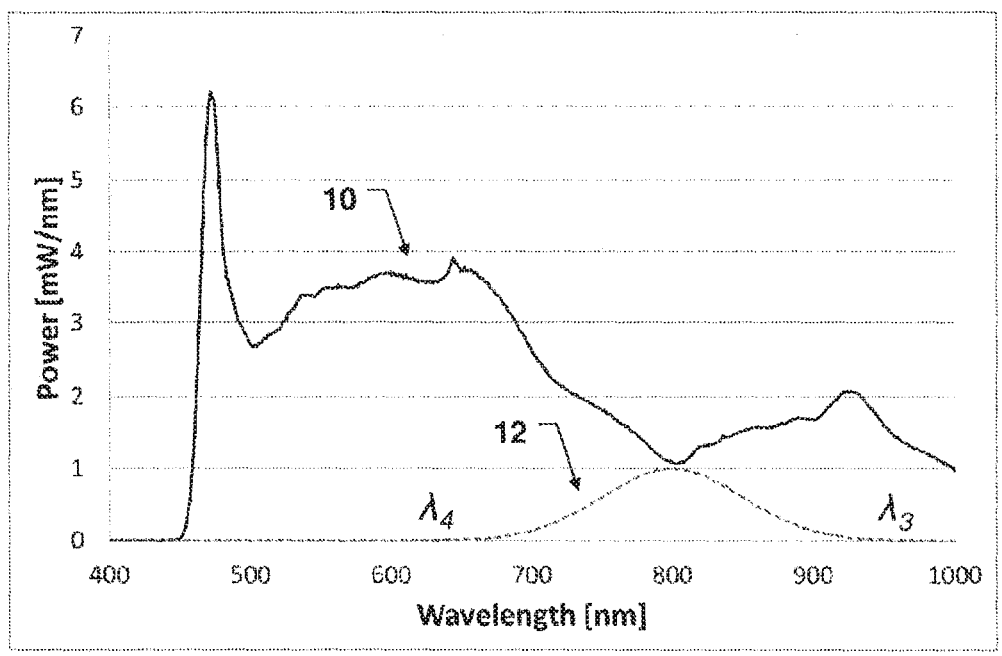
FIG. 3b shows an example of a supercontinuum spectrum output from the intermediate supercontinuum light source 100, as well as an example of the spectrum output from the single mode coupling unit 300, respectively.

FIG. 3*b* shows an example of a supercontinuum spectrum output from the intermediate supercontinuum light source 100 (spectrum 10), as well as an example of the spectrum output from the single mode coupling unit 300 (spectrum 12), respectively. In this example, the spectrum after the single mode coupling unit has a Gaussian distribution and is spanning from $\lambda_4$ being about 650 nm to $\lambda_3$ being about 950 nm. FIG. 3*b* thus shows that the spectral shape after the single mode coupling unit is different from the spectral shape in the same wavelength range from the intermediate supercontinuum source.

Figure 3C:
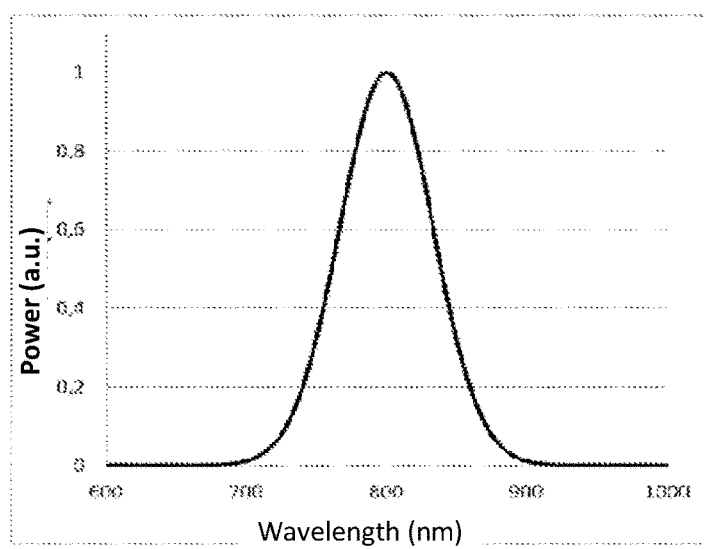
FIGS. 3c, 3d and 3e show exemplified spectra output from the single mode coupling unit.
Figure 3D:
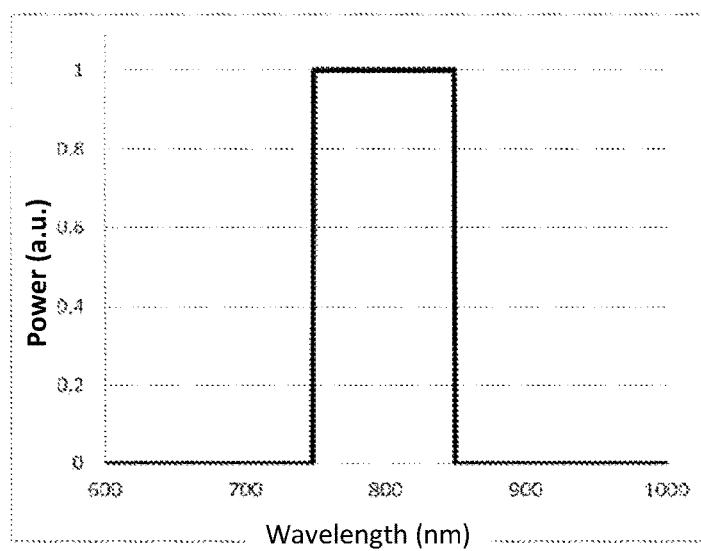
Figure 3E:
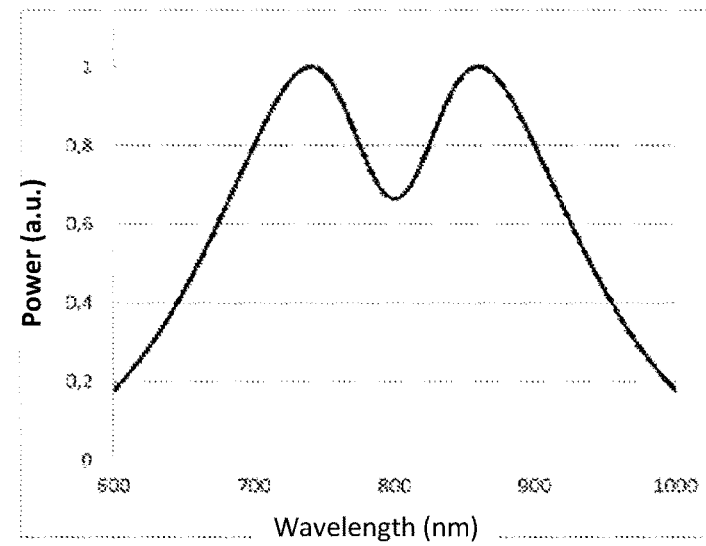

FIGS. 3*c*, 3*d* and 3*e* shows examples of the spectrum output from the single mode coupling unit 300, the spectral shapes being a Gaussian (FIG. 3*c*), a flat top (FIG. 3*d*) and a double peak distribution (FIG. 3*e*), respectively. A double peak distribution might be advantageous if the output from the light source is to be sent through an optical element with a Gaussian like transfer function (as e.g. an optical lens) prior to illuminating the object and it is advantageous to illuminate the object with a flat top distribution.

Figure 4A:
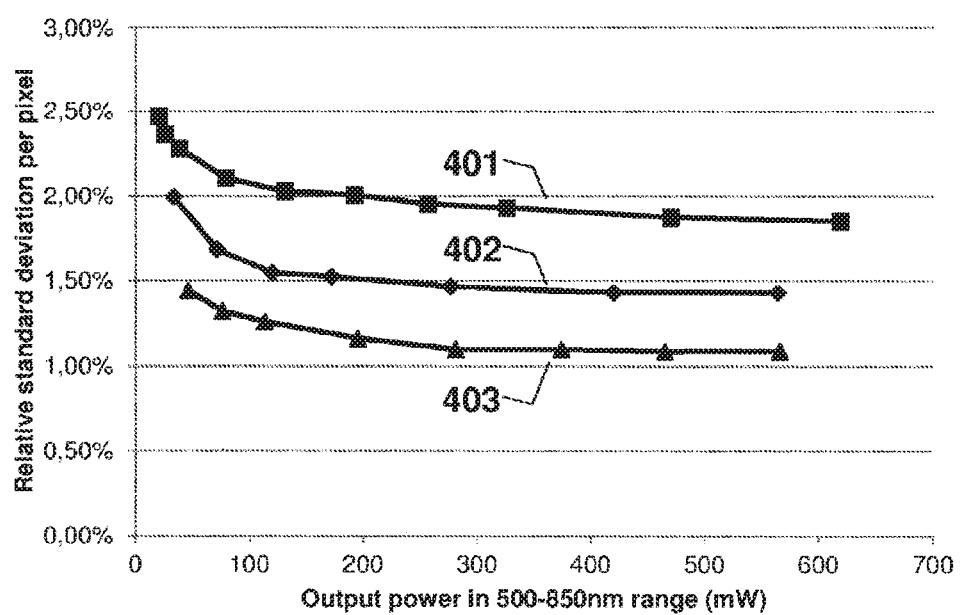
FIGS. 4a and 4b show the average intensity noise of an intermediate supercontinuum light source after and prior to compensation for spectrometer noise.
Figure 4B:
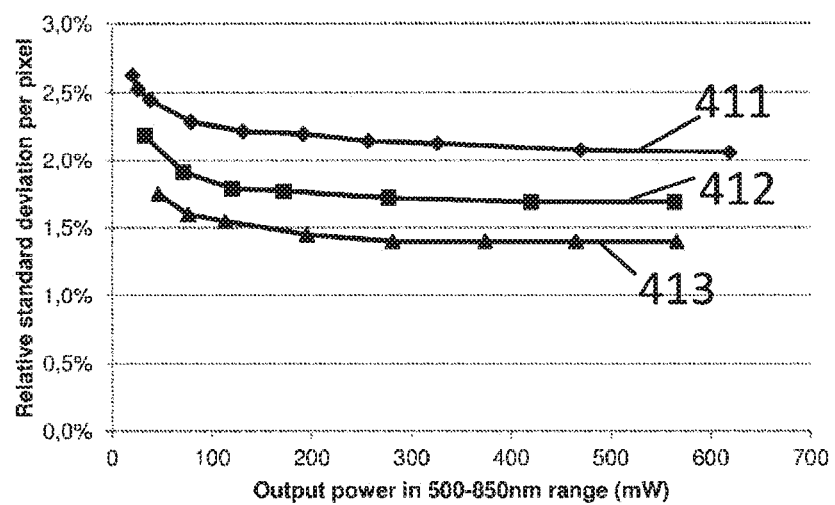

In one embodiment, the spectral shape after the single mode coupling unit is different from the spectrum in the same wavelength range from the intermediate supercontinuum source, such as a Gaussian, flat top or a double peak distribution. FIGS. 4*a* and 4*b* shows measurement result from a setup according to FIG. 3*a*. The intermediate SC light source was designed according to FIG. 1.

FIG. 4*a* shows the average intensity noise of an intermediate supercontinuum light source 100 (see FIG. 1) measured between 790-870 nm using a Wasatch Cobra UD spectrometer (310) with a Basler Sprint SPL4096-70 km camera as a function of power of the supercontinuum light source between 400 and 850 nm. FIG. 4*a* shows the average intensity noise after compensation for the spectrometer noise, whilst FIG. 4*b* shows the average intensity noise prior to compensation for the spectrometer noise. FIG. 4*a* contains measurements for three different pump pulses frequencies ($F_{pump}$) being 80 MHz (curve 401) 160 MHz (curve 402) and 320 MHz (curve 403). It is seen that the noise decreases when the pump pulse frequency increases. The intensity noise is compensated for the noise added by the spectrometer.

FIG. 4*b* shows the intensity noise data from FIG. 4*a*, prior to compensation for the noise from the spectrometer. FIG. 4*b* contains measurements for three different pump pulses frequencies ($F_{pump}$) being 80 MHz (curve 411), 160 MHz (curve 412) and 320 MHz (curve 413). Again, it is seen that the noise decreases when the pump pulse frequency increases.

The MO 101 is a mode-locked Yb-fiber laser with an output having a center wavelength at about 1060 nm and pulse duration around 6 ps. The laser is passively mode-locked via a SESAM and provides pulses with a repetition rate of 80 MHz. This laser type is well-suited for seeding because the all-fiber design provides a laser which is robust and relatively simple to produce relative to a bulk-optical setup. The maximum repetition rate is determined by how short the cavity can be made and the response properties of the SESAM. In practice these limitations often impose a practical upper limit to the repetition rate of about 100 MHz. In an embodiment, other gain media may be applied to provide other output wavelengths, and the pulse duration and repetition rate may also be altered within the limits discussed elsewhere.

In an embodiment, the seed laser is a fiber laser, such as a mode-locked fiber laser, such as mode-locked via a SESAM. The gain medium may be formed by any suitable laser gains medium such e.g. Yb-doped fiber, an Er-doped fiber and an Er/Yb-doped fiber. The seed laser may e.g. be a linear cavity laser or a ring laser.

The non-linear medium 107 is a microstructured PCF fiber formed by a silica core surrounded by a hexagonal pattern of holes arranged so that the core is formed by a missing hole in the pattern. The fiber is designed so that the ZDW of the fiber is relatively close to the pump wavelength so that substantial pump energy provided in the anomalous regime of the fiber.

As in FIG. 1 a set of optical fiber amplifiers 102,104 are arranged around an optional PFM. Without a PFM the pump system pumps the fiber with approximately 10 W, 8-10 ps at 80 MHz. By inserting a PFM according to FIG. 2*a* the repetition rate is increased to 160 MHz and by inserting a PFM according to FIG. 2*b* the repetition rate is quadrupled to 320 MHz. FIGS. 4*a* and 4*b* show experimental results obtained using a Wasatch Cobra UD spectrometer with Basler Sprint SPL4096-70 km camera arranged to measure the spectral range of 790-870 nm with 4096 pixels i.e. about 0.02 nm/pixel. A measurement time of 12.9 μs was applied and the fluctuation of the power measured at each pixel recorded. Long and short measurement times are possible such as between 1 μs and 1 ms or higher. Often, a short measurement time is desirable, such as for Fourier-domain OCT (see FIG. 4*b*) where real-time imaging is often required. In FIG. 4 the average relative standard deviation per pixel in the spectral range of 790-870 nm is measured as a function of the visible part of the spectrum. It is observed that the standard deviation and thus the intensity noise drops significantly as the repetition rate of the pump pulses is doubled, and further when it is quadrupled for equal amount of average power in the visible range. The amount of power in the visible range depends on how effectively the pump energy is converted to visible light which depends on the peak power of the pump pulses and the total amount of pump power (average power). In FIG. 4*a* the estimated noise contribution from the spectrometer has been subtracted, whereas this is included in FIG. 4*b*.

Figure 5:
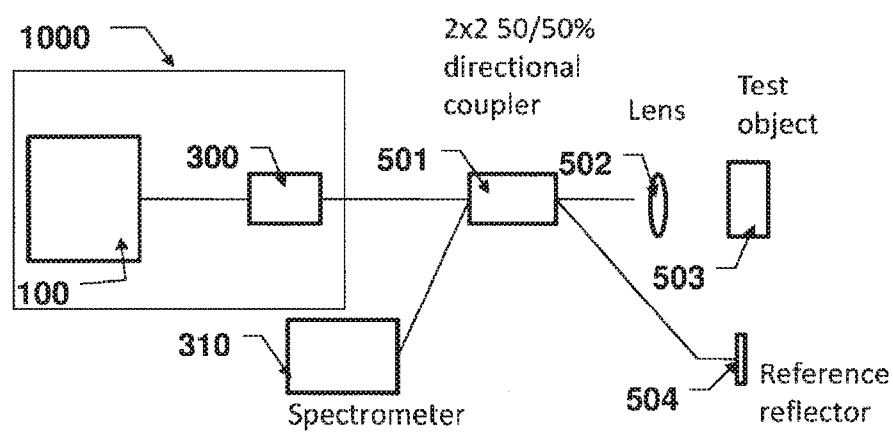
FIG. 5 shows an optical measurement system exemplified as an OCT system utilizing a SC light source as light source.

FIG. 5 shows an optical measurement system exemplified as an OCT system utilizing a SC source as light source. The system shown in FIG. 5 is a Fourier domain OCT (FD-OCT) system according to the invention where a SC light source 1000 is applied as light source thus being suitable for an optical measurement system according to the invention. A 2×2 50/50 directional splitter/coupler (501), coupled to the light source and spectrometer (310) acting as detection on one side and a lens (502), the object to be measured (503) and a reference reflector (504) on the other side, forms the interferometer core of the OCT system. A line scan (depth profile of the sample) is performed by a measurement of the spectrometer where the measurement depth is determined by the spectral resolution, and the spatial resolution in the sample is determined by the spectral width of the measurement. Often, the beam is scanned over the object to provide 2D or 3D depth profiles of the reflectivity in the sample. OCT is an extensive field comprising a large number of variations of the system configuration which are all expected to benefit from the aspects of the present invention. The output spectrum is preferably Gaussian so that in one embodiment the SM coupling unit is arranged to shape the spectrum from the SC light source into a Gaussian spectrum, such as the embodiments discussed in relation to FIG. 5a (single band Gaussian spectrum) and FIG. 6 (dual band Gaussian spectrum) in PCT/DK2011/050475 as well as FIG. 16 arranged to provide broad tunable spectra. In one embodiment, the SM coupling unit comprises a filter arranged to provide a Gaussian spectrum. The 50/50 coupler should be arranged to handle a wide spectrum and is typically either a fused fiber coupler or a bulk optical coupler.

Figure 6:
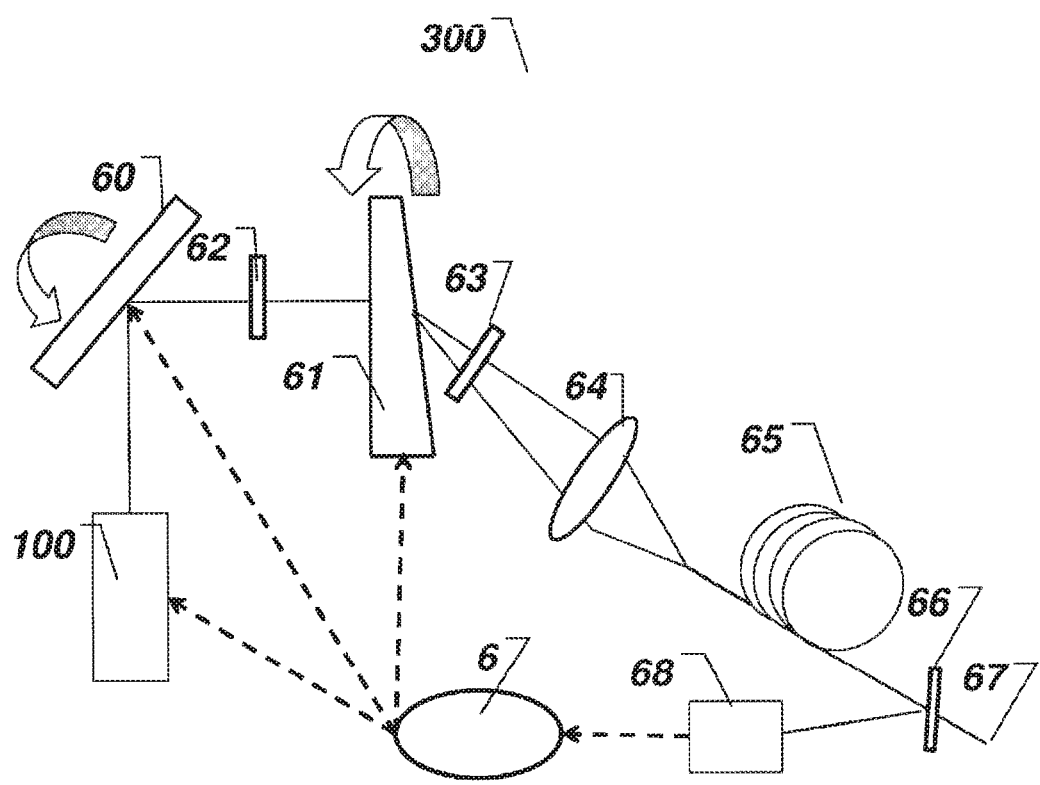
FIG. 6 shows an example of a single mode coupling unit comprising a dichroic element being a dichroic mirror, a dispersive element being a prism and a single mode fiber arranged to shape the spectrum.

FIG. 6 shows an example of a single mode coupling unit 300 comprising a dichroic element being a dichroic mirror, a dispersive element being a prism, and a single mode fiber arranged to shape the spectrum. Thus, FIG. 6 shows an example of how to construct the single mode coupling unit 300. The output of the intermediate supercontinuum light source 100 is directed to a dichroic element 60 and a dispersive element 61. Either the mirror and/or the angular dispersive element are connected to an electronic control 6, which enables a rotation between these two elements. The system might optionally also include a tunable dampening filter 62 and/or a tunable spatial filter 63. The light is collimated by a lens system 64 and collected by a fiber 65, which thereby is shaping the spectrum. The system might optionally include a broadband splitter 66, which sends a part of the light to the output 67 and another part of the light to a detector system 68. Said detector system is connected to the electronic control system 6, which again is connected to the supercontinuum light source 100 and/or the dichroic element 500 in order to stabilize the output power. In one embodiment, the dispersive element is a prism. In one embodiment, the fiber 65 is a single mode fiber, such as a step-index fiber or microstructured fiber. In one embodiment, the collimation lens system 64 comprises multiple lenses.

Figure 7:
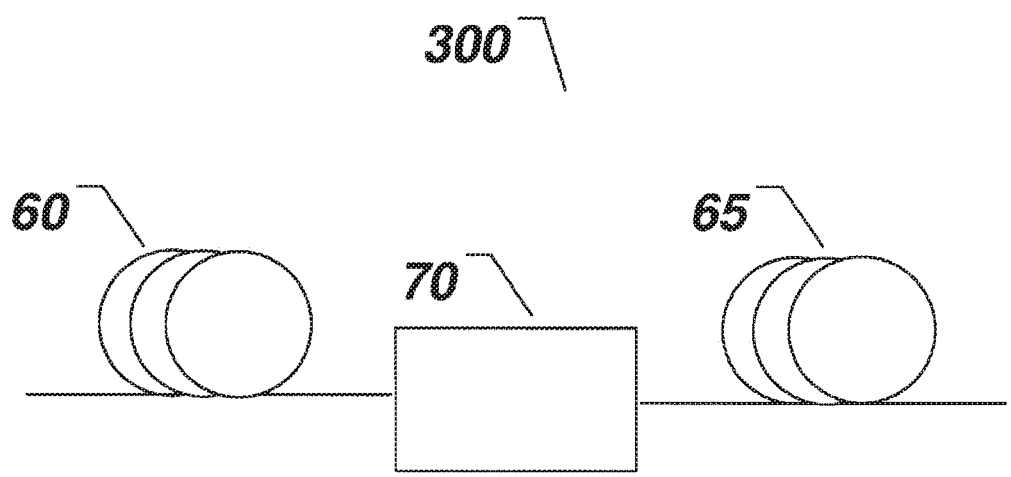
FIG. 7 shows an example of a single mode coupling unit comprising a dichroic element being a single mode fiber, a dampening and/or shaping optical element and a second single mode fiber.

FIG. 7 shows an example of a single mode coupling unit 300 comprising a dichroic element being a single mode fiber 60, a dampening and/or shaping optical element 70 and a second single mode fiber 65.

In one embodiment, the first single mode fiber 60 has a high loss above a certain threshold wavelength $\lambda_6$ and thus acts as a spectral filter. In one embodiment, the dampening and/or shaping optical element is selected from the list of a prism, an optical low-pass and optical high-pass and optical band-pass filter, a neutral density filter.

Figure 8A:
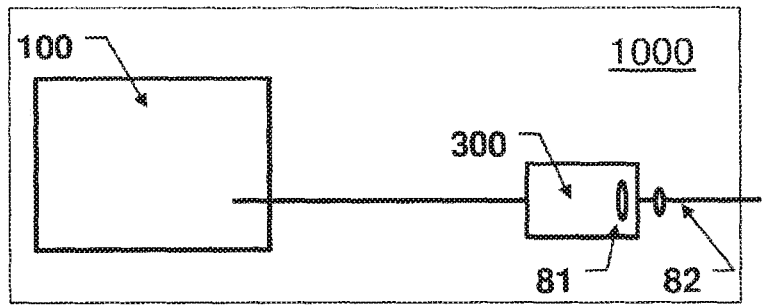
FIG. 8a-8c show three examples of how to dampen optical power.
Figure 8B:
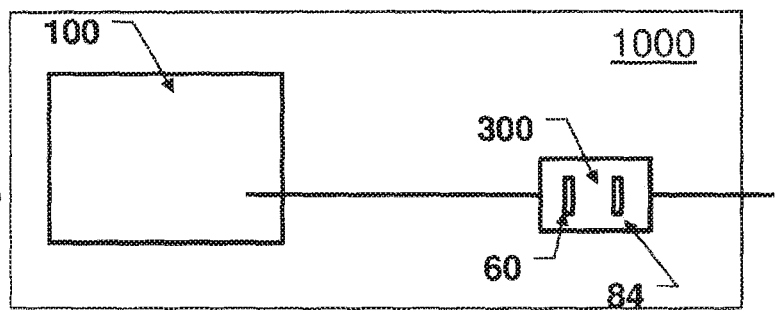
Figure 8C:
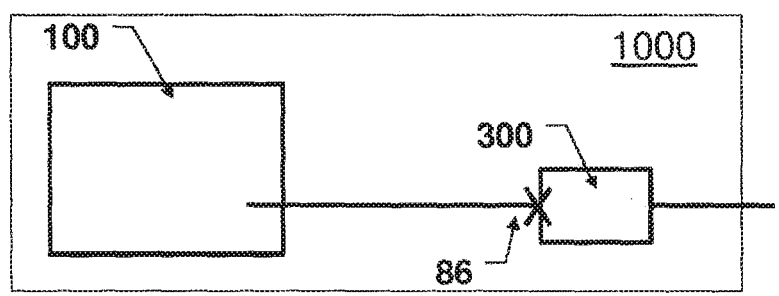

FIG. 8a-8c show three examples of how to dampen optical power in the supercontinuum light source of the invention.

In each of the FIGS. 8a to 8c, the supercontinuum light source is denoted by the reference number 1000, whilst the intermediate supercontinuum light source is denoted by the reference number 100 and the single-mode coupling unit by the reference number 300.

In FIG. 8a, the single mode coupling unit 300 comprises a dampening and shaping unit 81, where the mode field diameter at the output of the dampening and shaping unit 81 is different from the mode field diameter of a second single mode fiber 82. FIG. 8a thus shows mode field diameter mismatch at the output of the dampening and shaping unit 81 of the single mode coupling unit 300.

In FIG. 8b, the single mode coupling unit 300 comprises a dampening and shaping unit in the form of a shaping element 83 and a dampening element 84.

FIG. 8c shows an example where the dampening in the single mode coupling unit 300 is obtained by having an optical splice with large loss 86 between the intermediate supercontinuum source 100 and the input of the single mode coupling unit 300.

It should be emphasized that the term "comprises/comprising" when used herein is to be interpreted as an open term, i.e. it should be taken to specify the presence of specifically stated feature(s), such as element(s), unit(s), integer(s), step(s) component(s) and combination(s) thereof, but does not preclude the presence or addition of one or more other stated features.

Moreover, the term "substantially" is meant to include what is within the ordinary tolerances.

All features of the inventions including ranges and preferred ranges can be combined in various ways within the scope of the invention, unless there are specific reasons for not combining such features.

The invention claimed is:

1. A supercontinuum light source comprising:
   a seed laser configured to provide seed pulses with a pulse frequency $F_{seed}$;
   a pulse frequency multiplier (PFM) configured to multiply the seed pulses by converting seed pulses having the pulse frequency $F_{seed}$ to pump pulses with a pulse frequency $F_{pump}$, where $F_{pump}$ is larger than $F_{seed}$;
   a non-linear element configured to receive said pump pulses and convert said pump pulses to pulses of supercontinuum light; and
   first and second amplifiers, one of the amplifiers configured to amplify pulses having the pulse frequency $F_{seed}$ and the other of the amplifiers configured to amplify pulses having the pulse frequency $F_{pump}$;
   wherein said PFM is located between the amplifiers; and
   wherein said PFM comprises a splitter configured to split seed pulses into first and second sub beams, wherein the splitter has an uneven split ratio.

2. The supercontinuum light source of claim 1, wherein said PFM comprises an attenuator configured to attenuate pulses of light having a pulse frequency that is less than $F_{pump}$.

3. The supercontinuum light source of claim 1, wherein said PFM comprises a second splitter, said second splitter has a splitter ratio that is uneven.

4. The supercontinuum light source of claim 1, wherein said PFM comprises a delay line for delaying one of the first and second sub beams.

5. The supercontinuum light source of claim 1, wherein said PFM comprises an attenuator for attenuating one of the first and second sub beams.

6. The supercontinuum source of claim 1, wherein said non-linear element comprises a microstructured optical fiber.

7. The supercontinuum source of claim 1, wherein $F_{pump}$ is 150 MHz or more.

8. The supercontinuum light source of claim 1, wherein said seed laser is configured to provide seed pulses with a pulse duration $t_{seed}$ that is longer than about 1 ps.

9. The supercontinuum light source of claim 8, wherein $t_{seed}$ is shorter than about 50 ps.

10. The supercontinuum light source of claim 1, wherein the supercontinuum light source is configured such that the total average optical power in the range 400 nm-850 nm is less than 100 mW.

11. The supercontinuum light source of claim 1, wherein the amplifiers provide an increase in pulse energy and peak power relative to an output from the seed laser.

12. The supercontinuum light source of claim 1, wherein the supercontinuum light source is configured such that peak power of the pulses out of the first amplifier is constant.

13. The supercontinuum light source of claim 1, wherein the supercontinuum light source is configured such that peak power of the pulses out of the second amplifier is constant.

14. The supercontinuum light source of claim 1, wherein said seed laser comprises a mode locked Yb laser.

15. The supercontinuum light source of claim 14, wherein said mode locked Yb laser comprises a fiber laser that is passively mode locked via a SESAM (Semiconductor Saturable Absorber Mirror).

16. A supercontinuum light source comprising:
a seed laser configured to provide seed pulses with a pulse frequency $F_{seed}$;
a pulse frequency multiplier (PFM) configured to multiply the seed pulses by converting seed pulses having the pulse frequency $F_{seed}$ to pump pulses with a pulse frequency $F_{pump}$, where $F_{pump}$ is larger than $F_{seed}$;
a non-linear element configured to receive said pump pulses and convert said pump pulses to pulses of supercontinuum light; and
first and second amplifiers, one of the amplifiers configured to amplify pulses having the pulse frequency $F_{seed}$ and the other of the amplifiers configured to amplify pulses having the pulse frequency $F_{pump}$;
wherein said PFM is located between the amplifiers; and
wherein the supercontinuum light source is configured such that the pulses of supercontinuum light have a pulse duration and wherein an average optical power output from the supercontinuum light source is less than 5 Watt output per ps pulse duration.

17. The supercontinuum light source of claim 16, wherein said PFM comprises an attenuator configured to attenuate pulses of light having a pulse frequency that is less than $F_{pump}$.

18. The supercontinuum light source of claim 16, wherein said PFM comprises a splitter configured to split seed pulses into first and second sub beams, wherein the splitter has an uneven split ratio.

19. The supercontinuum light source of claim 16, wherein said PFM comprises a second splitter, said second splitter has a splitter ratio that is uneven.

20. The supercontinuum light source of claim 16, wherein said PFM comprises a delay line for delaying one of the first and second sub beams.

21. The supercontinuum light source of claim 16, wherein said PFM comprises an attenuator for attenuating one of the first and second sub beams.

22. The supercontinuum light source of claim 16, wherein said non-linear element comprises a microstructured optical fiber.

23. The supercontinuum light source of claim 16, wherein $F_{pump}$ is 150 MHz or more.

24. The supercontinuum light source of claim 16, wherein said seed laser is configured to provide seed pulses with a pulse duration $t_{seed}$ that is longer than about 1 ps.

25. The supercontinuum light source of claim 24, wherein $t_{seed}$ is shorter than about 50 ps.

26. The supercontinuum light source of claim 16, wherein the supercontinuum light source is configured such that the total average optical power in the range 400 nm-850 nm is less than 100 mW.

27. The supercontinuum light source of claim 16, wherein the amplifiers provide an increase in pulse energy and peak power relative to an output from the seed laser.

28. The supercontinuum light source of claim 16, wherein the supercontinuum light source is configured such that peak power of the pulses out of the first amplifier is constant.

29. The supercontinuum light source of claim 16, wherein the supercontinuum light source is configured such that peak power of the pulses out of the second amplifier is constant.

30. The supercontinuum light source of claim 16, wherein said seed laser comprises a mode locked Yb laser.

31. The supercontinuum light source of claim 30, wherein said mode locked Yb laser comprises a fiber laser that is passively mode locked via a SESAM (Semiconductor Saturable Absorber Mirror).

* * * * *